ns Patent [19]

Krumme et al.

[11] 4,311,911
[45] Jan. 19, 1982

[54] TOMOGRAPHIC APPARATUS FOR PRODUCING TRANSVERSE LAYER IMAGES

[75] Inventors: Hans-Jochen Krumme, Uttenreuth; Guenter Schmitt, Erlangen, both of Fed. Rep. of Germany

[73] Assignee: Siemens Aktiengesellschaft, Berlin & Munich, Fed. Rep. of Germany

[21] Appl. No.: 105,890

[22] Filed: Dec. 21, 1979

[30] Foreign Application Priority Data

Feb. 23, 1979 [DE] Fed. Rep. of Germany ....... 2907206

[51] Int. Cl.³ .............................................. A61B 6/00
[52] U.S. Cl. .................................................. 250/445 T
[58] Field of Search ................................... 250/445 T

[56] References Cited

U.S. PATENT DOCUMENTS 3,937,963 2/1976 Hounsfield ...................... 250/445 T

FOREIGN PATENT DOCUMENTS 2741874 3/1978 Fed. Rep. of Germany .

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a radiation-measuring arrangement comprises a radiation source which produces a fan-shaped beam of rays, and a radiation receiver which determines the radiation intensity behind the subject. The beam of rays executes a scanning movement in the layer plane for scanning a layer area which is greater than the layer area corresponding to the fan-shaped extent of the beam of rays. Furthermore, there is a rotating ring for the measuring arrangement for irradiating the radiography subject from different directions. The output signals of the radiation receiver are transformed by a measured value converter into a layer image. The measuring arrangement is mounted on a rotatable support which is pivotally mounted on the rotating ring and is swivelled by a drive element of a second rotating ring when the angular velocity of the second rotating ring differs from the angular velocity of the first rotating ring.

8 Claims, 1 Drawing Figure

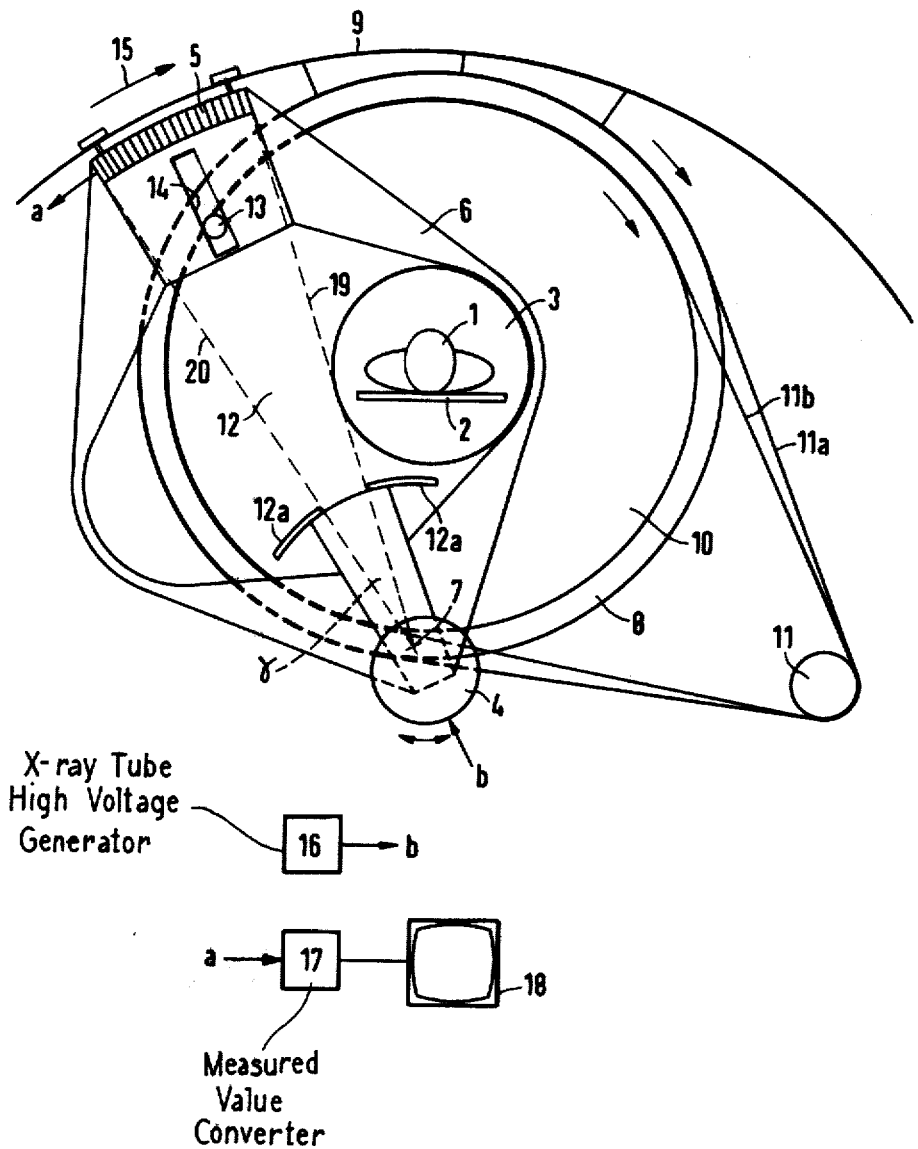

TOMOGRAPHIC APPARATUS FOR PRODUCING TRANSVERSE LAYER IMAGES

BACKGROUND OF THE INVENTION

The invention relates to a tomograph for producing transverse layer images of a radiography subject, having a radiation-measuring arrangement comprising a radiation source which produces a fan-shaped beam of rays which penetrates the radiography subject, its cross sectional dimension perpendicular to the layer plane being equal to the layer thickness, and also a radiation receiver which determines the radiation intensity behind the subject and which comprises a row of radiation detectors, having means for moving the beam of rays in the layer plane for the purpose of scanning a layer area which is greater than the layer area penetrated by the beam of rays, and also having a rotating ring for the measuring arrangement for irradiating the radiography subject from different directions, and having a measured value converter for transforming the signals supplied by the radiation receiver into a layer image.

A tomograph of this type is described in German Offenlegungsschrift No. 27 41 874. As the measuring arrangement rotates about the radiography subject, the layer to be examined of the radiography subject is scanned by the beam of rays. The radiation receiver supplies output signals from which a computer in the measured value converter calculates the attenuation coefficients of predetermined points of the layer examined. The attenuation coefficients calculated can then be reproduced in the form of a layer image on a monitor, for example a television monitor.

With the known tomograph, the beam of rays moves in the layer plane for the purpose of scanning a layer area which is greater than the layer area penetrated by the beam of rays, in that the radiation source and the radiation receiver are moved in opposite directions about an axis which passes through the layer area. For the purpose of moving the beam of rays, there is provided a collimator which is displaced in synchronism with the movement of the detector, the beam of rays emitted by the radiation source being collimated such that only the radiation receiver is impinged on by radiation. Specific gearing is necessary to displace the collimator. This implies high construction costs.

SUMMARY OF THE INVENTION

The object underlying the invention is to construct a tomograph of the type previously mentioned such that it is simpler and less susceptible to disorders relative to the prior art.

This object is achieved according to the invention in that the measuring arrangement is mounted on a rotatable support which is pivotally mounted on the rotating ring. With the tomograph according to the invention, in order to scan the radiography subject in the layer plane for the purpose of scanning a layer area which is greater than the layer area penetrated by the beam of rays, the entire measuring arrangement is pivoted as a unit about a pivot point. If the collimator is fixedly connected with the rotatable support, then displacement of the collimator relative to the radiation source is not necessary. Operation can thus take place using a collimator which is fixed relative to the source and detector, and mounted on a common support therewith.

A particularly advantageous and simple design is produced if two concentrically disposed rotating rings are provided, the outer one of which carries the pivot for the support, the pivot axis coinciding with the focus of the radiation source, and the inner one of which bears a driver for the pivotal support, and if the rotating rings are driven by a single motor via drive transmission means such that with rotation of the outer ring to execute a scanning cycle, the inner ring rotates relative to the outer ring through the desired angle (which at least corresponds to the aperture angle of the beam of rays).

The invention is described in greater detail in the following with the aid of an exemplary embodiment represented in the drawing; and other objects, features and advantages will be apparent from this detailed disclosure and from the appended claims.

BRIEF DESCRIPTION OF THE DRAWINGS

The single FIGURE of drawings is a diagrammatic end view of a tomographic apparatus in accordance with the present invention and indicating associated electric circuit components.

DETAILED DESCRIPTION

The drawing shows a patient 1 lying on a patient support 2. The patient 1 is positioned in an opening 3 of the apparatus, so that a desired transverse layer is scanned by a measuring arrangement comprising an x-ray tube 4 and a radiation receiver 5. The measuring arrangement 4, 5 is mounted on a rotatable support arm 6 which is pivotally mounted on a rotating ring 8 for pivotal movement about an axis 7 which passes through the focus of the x-ray tube 4. The arm 6 is guided at its free end by a guide track 9 which is secured to the rotating ring 8. The rotating ring 8 has a common axis of rotation with an inner rotating ring 10 having the opening 3. The rotating rings 8, 10 are driven by a single motor 11, namely such that when the rotating ring 8 rotates about 360° the rotating ring 10 rotates through an angle which is greater than 360° by the desired angle through which the beam of rays 12 emitted by the x-ray tube 4 is to sweep (for example an angle at least equal to the aperture angle ($\gamma$) of the fan-shaped beam). This is achieved by the different external diameters of the rotating rings 8, 10 which are driven by the motor 11 via toothed belts 11a, 11b. With a complete rotation of the rotating ring 8 the rotatable arm 6 is swivelled via a pin 13 through the desired angle for angularly shifting the beam of rays 12, from the position shown, in the direction of the arrow 15, so that the beam sweeps the layer to be examined of the patient 1. The pin 13 is mounted on the rotating ring 10 and is guided in an oblong slot 14 of the rotatable arm 6. The angle of aperture $\gamma$ of the beam of rays 12 (its cross sectional dimension perpendicular to the layer plane being equal to the layer thickness) is determined by collimator sections 12a which are mounted on support 6 and are pivotal therewith about axis 7.

The x-ray tube 4 is supplied with high voltage by an x-ray tube high voltage generator 16 via an electrical connection indicated at b. The radiation receiver 5 comprises a row of detectors which converts the x-radiation received into corresponding electrical signals. These signals are supplied via a connection indicated at a to a measured value converter 17 which calculates the attenuation coefficients of predetermined points of the layer examined and effects pictorial reproduction of this layer on a television monitor 18. Advantageously, both the transfer of measured values from the radiation receiver 5 to the measured value converter 17 and the supply of high voltage to the x-ray tube 4 take place in a contact-free manner via rotating transmitters.

For scanning the transverse layer to be examined of the patient 1, the rotating ring 8 is rotated one or more times through 360°. The beam of rays 12 is dimensioned relative to the apparatus opening 3 such that in an initial position the defining ray 19 is disposed at one edge of apparatus opening 3 as shown in the drawing, while in the final position the defining ray 20 is disposed at the other edge of the apparatus opening 3 (i.e. the right-hand edge of opening 3 as viewed in the drawing). Concurrently, with the rotation of the rotatable ring 8, the beam of rays 12 is swivelled through the desired angle. The number of rotations is selected such that the entire radiography subject or the entire subject area to be radiographed is swept by the beam of rays 12.

The starting position for scanning can be adapted to the respective, maximum subject diameter. For example, for radiographing the head of the patient 1, before the actual measurement, the rotating rings 8, 10 can be rotated, with radiation switched-off, to such an extent that when measurement commences, the defining ray 19 is tangential to the head on the left. Calibration of the system can also be effected in this position. In this case, a measuring operation is terminated when the defining beam 20 is tangential to the head on the right. The smaller the subject, the quicker a measuring operation is thus concluded.

With small subjects and subject sections whose lateral dimension fits within the lateral extent of the beam of rays 12 (e.g. as defined by collimator 12a), the rotating rings 8, 10 can be rotated until the beam of rays 12 encompasses the layer to be scanned and is disposed in approximate symmetry with such layer. In this starting position for measuring, the pin 13 is disengaged from the rotating arm 6 (e.g. by its removal from ring 10), and the arm 6 is fixedly secured with the rotating ring 8. In this case a measurement is terminated at the earliest following one rotation of the rotatable ring 8.

Analogously, this measuring method is suitable practicable for staring positions of the beam of rays 12 between the symmetrical position described above and the limiting case in which a defining ray 19 in the starting position passes through the axis of rotation, in which limiting case the pivot angle for the beam coincides with its aperture angle $\gamma$.

In the exemplary embodiment the difference between the angular velocities of the rotating rings 8 and 10 is constant. Within the scope of the invention it is also possible to provide gearing means, for example gear-shifts, with which this difference can be altered and thus the angle covered by the beam of rays 12 per revolution of the rotating ring 8 can be adjusted. An optimum relation between image resolution and scanning velocity can thereby be set.

It will be apparent that many modifications and variations may be effected without departing from the scope of the novel concepts and teachings of the present invention.

We claim as our invention:

1. Tomographic apparatus for producing transverse layer images of a radiography subject, having a radiation measuring arrangement comprising a radiation source which produces a fan-shaped beam of rays which penetrate the radiography subject and exhibiting an aperture angle ($\gamma$), the cross sectional dimension of the beam perpendicular to the layer plane being substantially equal to the layer thickness, and also comprising a radiation receiver with a row of radiation detectors which determines the radiation intensity behind the subject, and having beam shifting means for moving the beam of rays in the layer plane for the purpose of scanning a layer area which is greater than the layer area penetrated by the fan-shaped extent of the beam of rays, and also having a rotatable ring mounting the measuring arrangement for rotational movement to irradiate the radiography subject from different directions, and having a measured value converter for transforming the signals supplied by the radiation receiver into a layer image, the beam shifting means comprising a rotatable support (6) which is pivotally mounted on the rotatable ring (8) for producing pivotal movement of the measuring arrangement (4, 5), characterized in that the beam shifting means comprises a swivel joint (7) for the rotatable support and a beam shifting ring (10) disposed concentrically with said rotatable ring (8), one ring (8) carrying the swivel joint (7) and the other ring (10) having a drive element (13) for pivoting said rotatable support (6) about said swivel joint (7), and means whereby the rings are driven at different angular velocities to effect shifting movement of the rotatable support (6) relative to said rotatable ring (8).

2. Tomographic apparatus according to claim 1, characterized in means for driving the rings (8, 10) such that with rotation of the ring (8) bearing the swivel joint (7) the ring (10) bearing the drive element (13) is rotated relative thereto through an angle at least equal to the aperture angle $\gamma$ of the beam of rays (12).

3. Tomographic apparatus according to claim 1, characterized in that the drive element (13) is detachable and the rotatable support (6) can be secured for rotation with the ring (8) bearing the swivel joint (7) so as to be locked against pivotal movement.

4. Tomographic apparatus according to claim 1, characterized in that the rotatable ring (8) bears the swivel joint (7) and the beam shifting ring (10) bears the drive element (13).

5. Tomographic apparatus according to claim 4, characterized in that the drive element (13) is a pin, the rotatable support (6) having an oblong hole (14) receiving said pin (13) to effect rotation of said support (6) relative to said rotatable ring.

6. Tomographic apparatus according to claim 1, characterized in that a single motor (11) is coupled with said rings (8, 10) and has gearing means (11a, 11b) for driving said rings at different angular velocities.

7. Tomographic apparatus according to claim 6, characterized in that the gearing means for setting the ratio of the angular velocities of the rings (8, 10) are adjustable.

8. Tomographic apparatus for producing transverse layer images of a radiography subject, having a radiation measuring arrangement comprising a radiation source which produces a fan-shaped beam of rays which penetrate the radiography subject and exhibiting an aperture angle ($\gamma$), the cross sectional dimension of the beam perpendicular to the layer plane being substantially equal to the layer thickness, and also comprising a radiation receiver with a row of radiation detectors which determines the radiation intensity behind the subject, and having beam shifting means for moving the beam of rays in the layer plane for the purpose of scanning a layer area which is greater than the layer area penetrated by the fan-shaped extent of the beam of rays, and also having a rotatable ring mounting the measuring arrangement for rotational movement to irradiate the radiography subject from different directions, and having a measured value converter for transforming the signals supplied by the radiation receiver into a layer image, the beam shifting means comprising a rotatable support (6) which is pivotally mounted on the rotatable ring (8) for producing pivotal movement of the measuring arrangement (4, 5), characterized in that the beam shifting means comprises means (10, 11, 11a, 11b, 13, 14) for pivoting the rotatable support (6) such that the rotatable support (6) can be pivoted at least through an angle corresponding to the aperture angle ($\gamma$) of the beam of rays (12), and in that in an initial position of the rotatable support (6) one defining ray (19), and in a final position of the rotatable support the other defining ray (20) of the beam of rays (12) is disposed at a respective edge of an apparatus opening (3) which receives the radiography subject (1).

* * * * *